United States Patent [19]
Corn

[11] Patent Number: 5,577,693
[45] Date of Patent: Nov. 26, 1996

[54] ANESTHESIA CIRCUIT STAND

[75] Inventor: Stephen B. Corn, Boston, Mass.

[73] Assignee: Children's Medical Center Corporation, Boston, Mass.

[21] Appl. No.: 371,019

[22] Filed: Jan. 11, 1995

[51] Int. Cl.$^6$ .................................................. F16M 11/00
[52] U.S. Cl. .................................. 248/176.1; 248/309.2; 248/80; 128/910
[58] Field of Search .................. 248/176.1, 309.2, 248/80; 128/910, 202.27

[56] References Cited

U.S. PATENT DOCUMENTS

| | | | |
|---|---|---|---|
| 3,310,267 | 3/1967 | Koehler | 248/176.1 |
| 3,357,666 | 12/1967 | Smith et al. | 248/309.2 |
| 3,370,805 | 2/1968 | Barbee | 248/309.2 |
| 3,814,091 | 6/1974 | Henkin | 128/188 |
| 3,938,551 | 2/1976 | Henkin | 137/613 |
| 4,051,847 | 10/1977 | Henkin | 128/145.6 |
| 4,332,244 | 6/1982 | Levy et al. | 128/205.25 |
| 4,506,665 | 3/1985 | Andrews et al. | 128/202.27 |
| 4,520,809 | 6/1985 | de Greef et al. | 128/200.24 |
| 4,633,890 | 1/1987 | Carden | 128/910 |
| 5,188,328 | 2/1993 | Thompson | 248/309.2 |
| 5,209,694 | 5/1993 | Utt, Jr. | 248/176.1 |

*Primary Examiner*—Alvin C. Chin-Shue
*Assistant Examiner*—Brian J. Hamilla
*Attorney, Agent, or Firm*—Thomas J. Engellenner; Lahive & Cockfield

[57] ABSTRACT

An anesthesia circuit stand is able to support an anesthesia circuit fitting, when not attached to a patient or to a patient airway securement device in such a manner that anesthesia vapor and nitrous oxide is prevented from escaping into the environment of an operating room. The stand includes a base portion to which is connected a stalk element. The stalk can be substantially in the form of a cone having a proximal end with a greater diameter than a distal end. Alternatively, the stalk can be in the shape of a generally cylindrical rod. A distal end of the stalk includes a plug portion which has a diameter sufficient to engage the inner diameter of an outlet orifice of an anesthesia circuit elbow in a frictional fit.

11 Claims, 5 Drawing Sheets

ANESTHESIA CIRCUIT STAND

BACKGROUND OF THE INVENTION

The invention relates to devices that minimize the pollution of operating rooms with anesthesia gases. More particularly, the invention relates to devices that prevent anesthesia gases from escaping from anesthesia circuit fittings during periods in which the anesthetic circuit is not attached to a patient's airway or to an airway securement device.

Surgical procedures often require the administration of a general anesthesia to a patient. In many instances the anesthesia is delivered with a gas through an anesthesia mask that is applied over a patient's nose and mouth. Recent reports indicate that the atmosphere within operating rooms during surgical procedures often contains potentially harmful levels, as much as 12 to 40 times the NIOSH recommended limit, of volatile anesthetic vapor and nitrous oxide gas. Studies have suggested that chronic exposure to trace levels of anesthetic gas is harmful to operating room personnel. Exposure to nitrous oxide causes decreased mental performance, audio-visual ability, and manual dexterity. It is also believed that exposure to high levels of nitrous oxide in the workplace can cause reduced fertility, spontaneous abortions, and neurologic, renal and liver disease. See, *Anesthesiology News*, October 1994.

Standard anesthesia procedures utilize an anesthesia machine to deliver an anesthetic gas mixture through an anesthesia circuit, attached to a mask or other airway securement device, such as an endotracheal tube (ETT) or laryngeal mask airway (LMA), to the patient. Initially, the anesthesia machine delivers oxygen to preoxygenate the patient. Then the machine adds the anesthetic vapor and nitrous oxide gas to the oxygen stream. When the patient is sufficiently anesthetized, the anesthetic gas supply is shut off and, in order to intubate the patient with an airway securement device, the mask is removed from the patient's face and often simply laid open on a convenient surface. During the time interval between the removal of the mask and the reconnection of the circuit fittings to the emplaced ETT or LMA, the flow of oxygen continues from the anesthesia machine directly into the operating room atmosphere. The oxygen is not pure, however. Although the supply of anesthetic gases has been shut down at the anesthesia machine, residual gases continue to be swept out by the oxygen flow. Because of the time constants of anesthetic elimination from the circuit, as much as 16 minutes can elapse before this release of residual anesthetic gases to the operating room environment is reduced to negligible levels. It is this release of the residual anesthetic gases which creates the hazards to operating room personnel.

Since it is necessary to use anesthetic circuits for anesthesia delivery, steps must be taken to reduce the dangers presented to operating room personnel through such techniques. At the same time, care must be taken not to compromise the operation and performance of the anesthesia circuit.

Accordingly, it is an object of the invention to provide a device to prevent the unintended pollution of operating rooms with anesthesia gases. A further object is to provide such a device that conveniently supports an anesthesia delivery mask and an anesthesia circuit fitting while preventing the escape of gas into the operating room environment. Another object of the invention is to provide such a device that does not alter the structure of or affect the performance of the anesthesia circuit. It is also an object to provide a device that enables an anesthesiologist to remove with greater ease an anesthesia delivery mask from an anesthetic circuit fitting. These and other objects will be apparent upon reading the description that follows.

SUMMARY OF THE INVENTION

The present invention provides a device for supporting an anesthetic circuit during surgical procedures, while preventing the escape of anesthesia gases into the operating room. This invention includes a base that enables the device to be securely mounted to a stable surface from which a stalk element extends. A distal end of the stalk includes a plug portion, generally cylindrical in shape, wherein the diameter of the plug portion is sufficient to fit within the inner diameter of the outlet orifice of a standard anesthetic circuit elbow. The plug portion of the stalk engages the outlet orifice of the anesthetic circuit elbow in a friction fit to prevent the escape of anesthetic gases from the anesthetic circuit. In one embodiment, the stalk can be of a cylindrical shape along its entire length. In another embodiment, the stalk is of a substantially conical shape, such that a proximal (or base) end of the stalk has a diameter that is greater than the distal end of the stalk. In this embodiment the distal end of the stalk can be substantially flat or can form the apex of a cone.

The invention also provides a method for preventing the escape of anesthesia gases into the environment of an operating room.

DETAILED DESCRIPTION OF THE INVENTION

As noted above, the present invention provides a support stand for an anesthetic circuit fitting that is able to support the anesthetic circuit fitting during periods that the anesthetic circuit is not attached to a patient's airway or to an airway securement device. While supporting the anesthesia circuit fitting the support stand also prevents the escape of anesthesia gas into the environment of an operating room.

Figure 1:
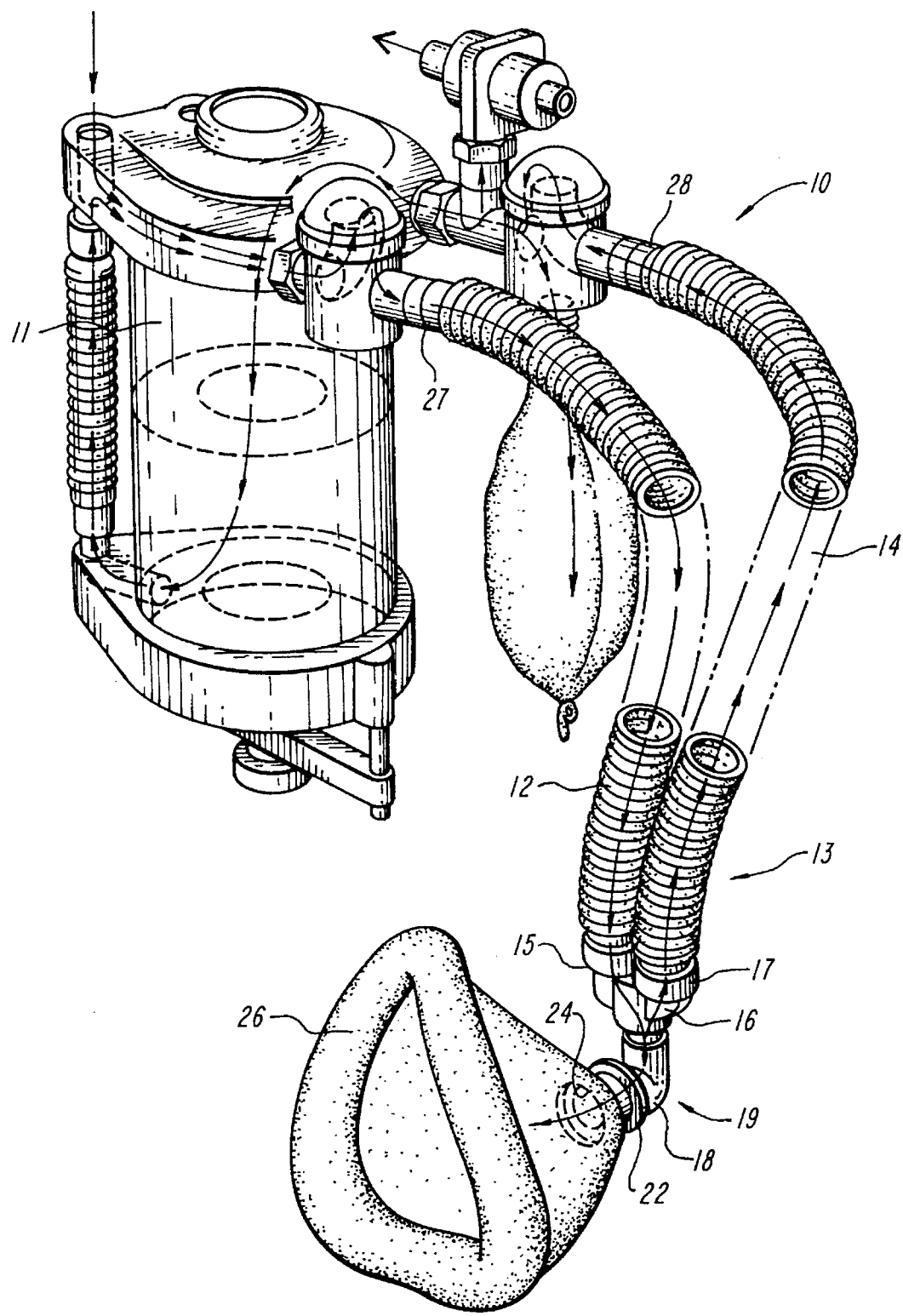
FIG. 1 is a perspective view of a standard, prior art anesthesia circle system, including an anesthesia delivery circuit and an anesthesia delivery mask.

FIG. 1 illustrates a standard, prior art anesthesia delivery system 10. The anesthesia delivery system 10 includes an anesthesia circle system gas delivery system 11 and an anesthetic circuit 13. The anesthetic circuit 13 includes a conduit 12 which forms the inhalatory limb, and a separate conduit 14 which forms the exhalatory limb 14 of the circuit. The inhalatory and exhalatory limbs 12, 14 each have outlet ends 15, 17 that engage a Y-connector 16. The Y-connector 16 attaches to an anesthesia circuit elbow 19. An outlet conduit 18 of the anesthesia circuit elbow 19 includes an outlet orifice 22 that fits within the inner diameter of a similarly shaped mask orifice 24 disposed within an anesthesia delivery mask 26. The inlet ends 27, 28 of the inhalatory and exhalatory limbs 12, 14 are connected to the anesthesia circle system gas delivery system 11.

Figure 2:
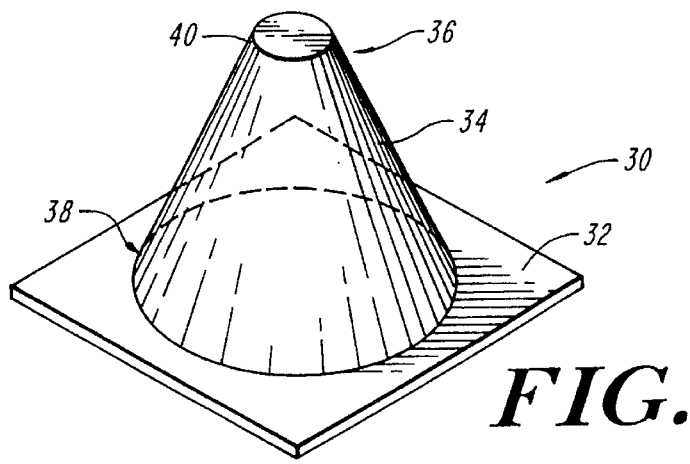
FIG. 2 is a perspective view of an anesthesia circuit stand according to one embodiment of the present invention.
Figure 2A:
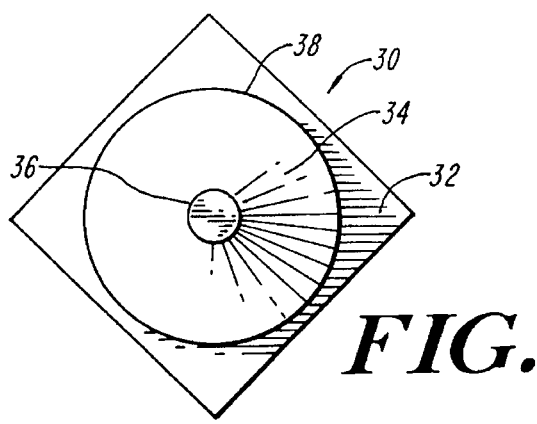
FIG. 2A is a top view of the device shown in FIG. 2.
Figure 3:
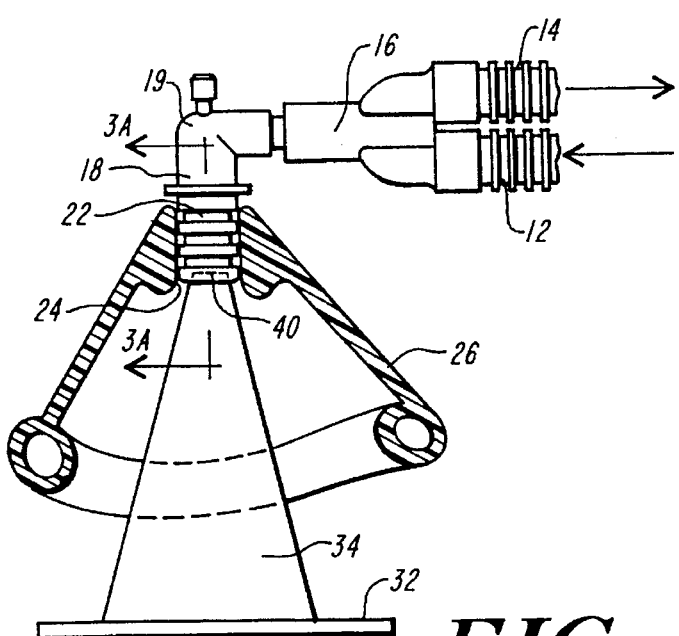
FIG. 3 is a cross-sectional view of the device of FIG. 2, illustrating its use in supporting an anesthesia delivery circuit and an anesthesia delivery mask.

As illustrated in FIGS. 2, 2A and 3, anesthesia circuit stand 30 includes a base portion 32 and a stalk element 34. The stalk element 34 includes a distal end 36 and a proximal end 38. The distal end 36 of stalk element 34 preferably includes a plug portion 40. Plug portion 40 preferably is substantially cylindrical in shape, having a constant diameter. Alternatively, the diameter of the plug portion 40 can be tapered such that a more distal end of the plug portion 40 has a diameter smaller than a more proximal end thereof. Preferably, the plug portion 40 is circular in cross section.

The diameter of the plug portion 40 preferably is such that it is able to be inserted within the inner diameter of the outlet orifice 22 of an anesthesia circuit elbow 19. The engagement between the plug portion 40 and orifice 22 is a friction fit that is sufficient to prevent the leakage of gas from outlet orifice 22. When the outlet orifice 22 is occluded by plug portion 40 gas that is passed through inhalatory limb 12 is prevented from entering the adjacent environment through outlet orifice 22. Instead, any anesthesia gases are recovered through exhalatory limb 14 due to the pressure differential that exists between inhalatory limb 12 and exhalatory limb 14.

Figure 3A:
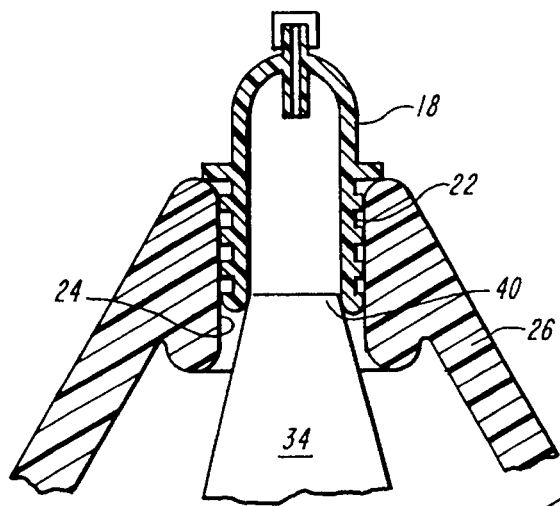
FIG. 3A is a sectional view of a portion of the device shown in FIG. 3, at lines 3A—3A.

FIG. 3A further illustrates the manner in which the outlet orifice 22 of the anesthesia circuit elbow 19, the anesthesia circuit delivery mask 26, and the stalk element 34 are engaged with one another. Mask 26 includes a mask orifice 24 having a substantially circular shape. The inside diameter of mask orifice 24 is less than the outer diameter of outlet orifice 22. Accordingly, the mask orifice 24 is placed over the outlet orifice 22 in a secure, friction fit to join mask 26 to anesthesia circuit fitting 13. The anesthesia circuit fitting having the attached mask 26 is mounted upon the stalk element 34 by inserting the mask 26 over the stalk element 34 to an extent sufficient to allow the plug portion 40 of stalk 34 to fit within the inner diameter of outlet orifice 22 in a friction fit.

Figure 4A:
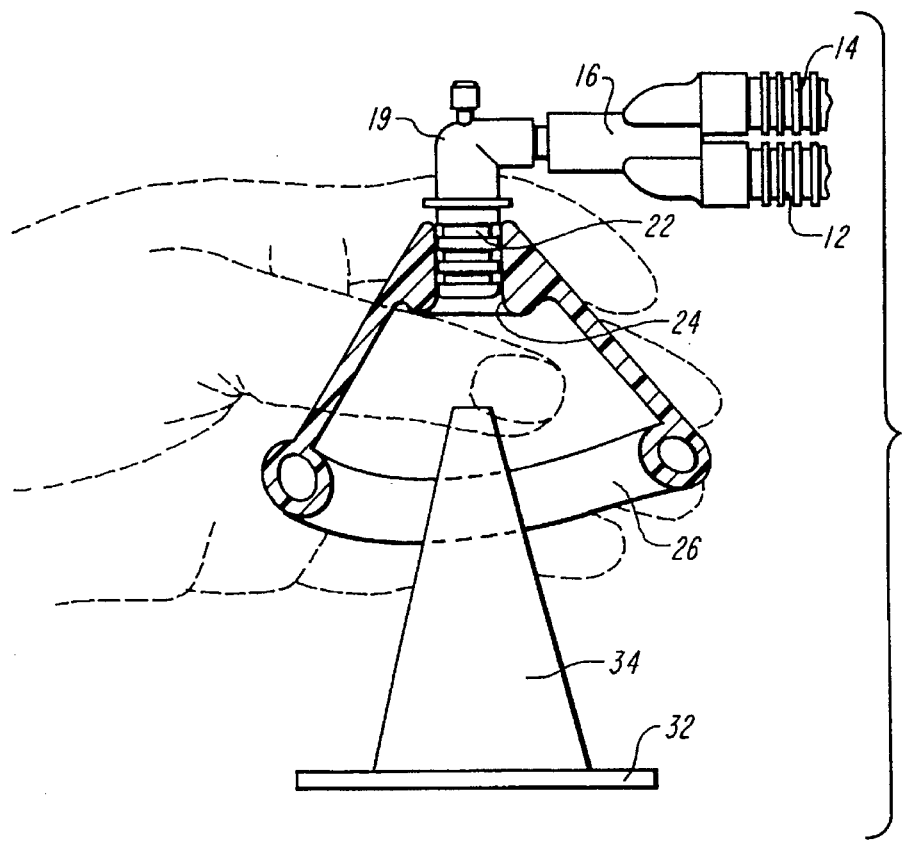
FIGS. 4A through 4D schematically illustrate the use of the device of FIG. 2 in supporting and manipulating an anesthesia circuit fitting.
Figure 4B:
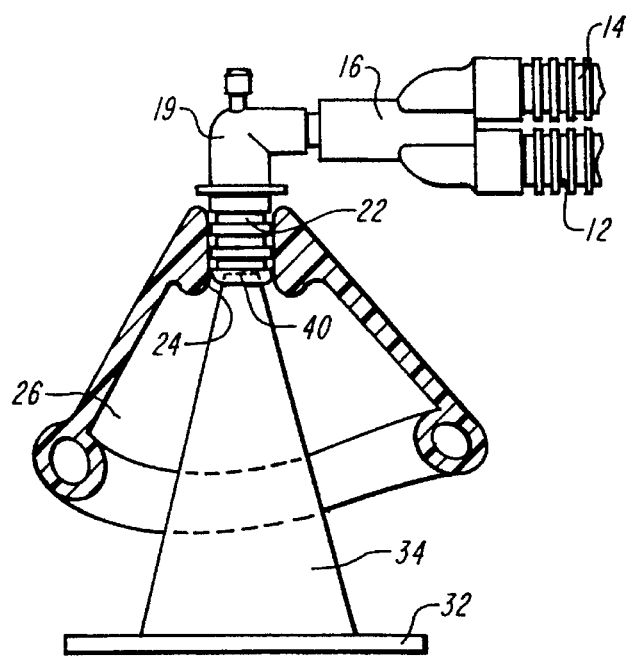

FIGS. 4A through 4D illustrate the use of the anesthesia circuit stand of the present invention. During a surgical procedure a patient is pre-oxygenated using the assistance of an anesthetic circuit fitting equipped with a mask 26. Thereafter, the anesthesia machine is activated to deliver nitrous oxide and a volatile anesthetic to a patient through the inhalatory limb 12 of the anesthesia circuit fitting 13. After the delivery of a desired amount of gaseous anesthetic, the anesthesia vaporizer and nitrous oxide delivery systems are turned off and the mask 26 is removed from contact with the patient and inserted over the stalk element 34 such that plug portion 40 is engaged by a frictional fit within outlet orifice 22 as shown in FIG. 4B. As so assembled, any anesthetic gas that continues to be delivered by the anesthesia machine is not able to exit through outlet orifice 22. Instead, the gas is recovered through the exhalatory limb 14 of the anesthesia circuit.

Figure 4C:
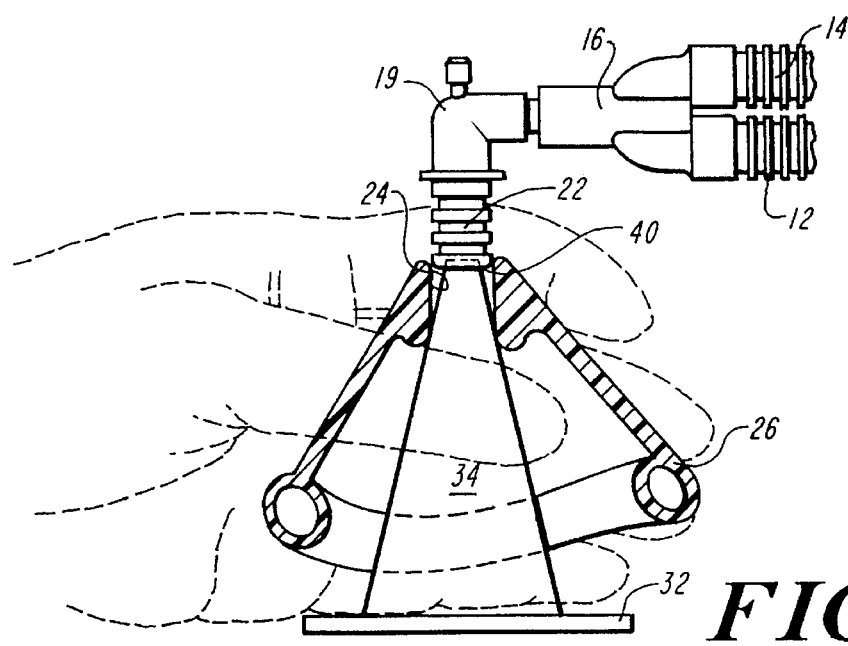
Figure 4D:
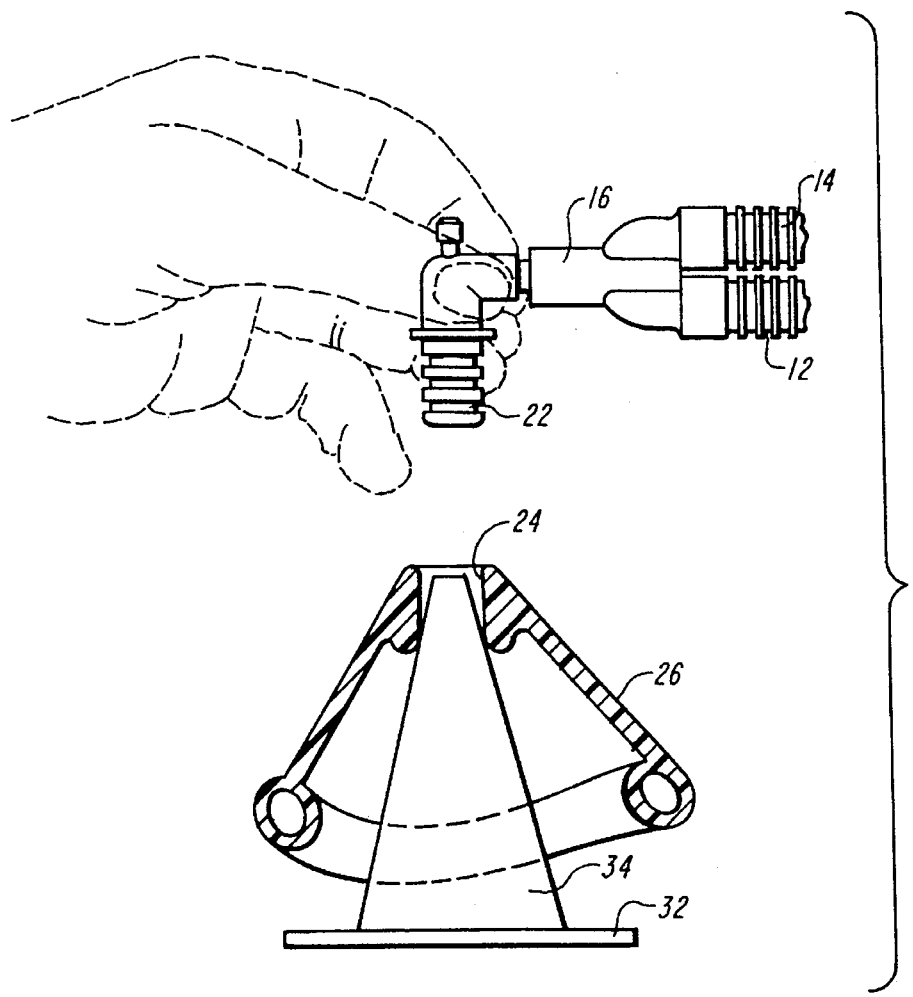

With the mask 26 removed from contact with the patient it is possible to place an endotracheal tube (not shown) within the patient's airway. After insertion of the endotracheal tube (not shown) within the patient's airway, the mask must be separated from the anesthetic circuit 13. Normally this is a procedure that requires an anesthesiologist to use two hands to separate the mask from the anesthesia circuit. As shown in FIG. 4C, however, the present invention enables this procedure to be performed while using one hand and, advantageously, enabling the anesthesiologist to maintain a grasp on the endotracheal tube. Separation of the mask from the anesthesia circuit is thus accomplished simply by pressing down, with one hand, on the mask alone, thus separating the mask from frictional engagement with outlet orifice 22 as the mask is moved to a lower position on stalk element 34 as shown in FIG. 4C. Once the mask 26 and the anesthesia circuit are fully separated, the anesthetic circuit elbow 19 can be removed from the stalk simply by lifting the circuit with one hand as shown in FIG. 4D to disengage the frictional fit between the outlet orifice 22 and plug portion 40.

The base 32 of anesthesia circuit stand 30 can be integral with the proximal end 38 of stalk element 34. Alternatively, the base 32 can be attachable to the proximal end 38 of stalk 34. One of ordinary skill in the art will appreciate that base 32 can take a variety of forms. For example, base 32 may be in the form of a platform that is separately mountable (such as by screws) to another surface, such as a table. The base may also be in the form of a support device that allows the stalk 34 to be securely affixed to a wall or to an anesthesia machine.

One of ordinary skill in the art will also appreciate that the dimensions of many elements of the anesthesia circuit stand of the invention may be varied. However, perhaps the most critical dimension of the anesthesia circuit stand 30 of the present invention is the diameter of the plug portion 40 of stalk 34. As noted above, the diameter of plug 40 must be such that it is able to be disposed within the inside diameter of anesthetic circuit elbow outlet orifice 22 in a frictional fit. This engagement should be sufficiently tight to prevent the escape of anesthesia gas from the seal between these two components. As standard anesthetic circuit elbows have orifices with an inside diameter of approximately 11.5 millimeters, the diameter of plug portion 40 preferably is approximately 10.8 to 11.3 millimeters.

In one embodiment the diameter of plug portion 40 should remain substantially constant along a length of the plug portion of about 1.5 to 3.0 centimeters. Alternatively, the diameter of the stalk 34 can gradually increase in a direction away from the distal end of stalk 34. In this embodiment the diameter of plug portion 36 should not exceed about 11.5 millimeters for a distance of about 1.5 centimeters from the distal end of the stalk.

In another embodiment the stalk element 34 is of a substantially conical shape such that the diameter at the distal end 36 that is less than the diameter at the proximal or base end 38. Preferably, the base diameter is in the range of about 23 to 30 mm. Also, the length of the stalk, although not critical, typically is approximately 7 to 12 cm. Those having ordinary skill in the art will readily appreciate that these dimensions can be modified as deemed necessary by one of ordinary skill in the art.

Figure 5:
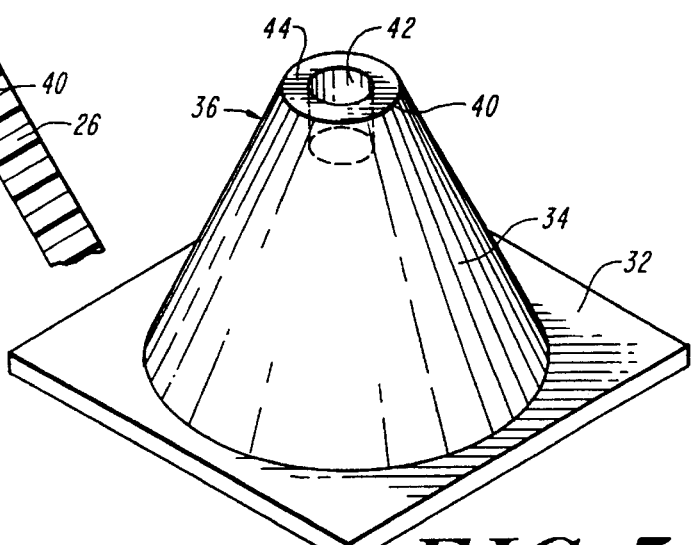
FIG. 5 is a schematic view of an alternative embodiment of the anesthesia circuit stand of FIG. 2.

FIG. 5 illustrates an embodiment of the invention in which distal end 36 of stalk 34 includes a cavity 42. The cavity 42 preferably is configured of suitable dimensions to hold a syringe, such as 10 cc syringe. The cavity preferably is cylindrical in shape having a diameter of approximately 2 to 4 mm and a depth of about 3 to 5 mm.

Figure 6:
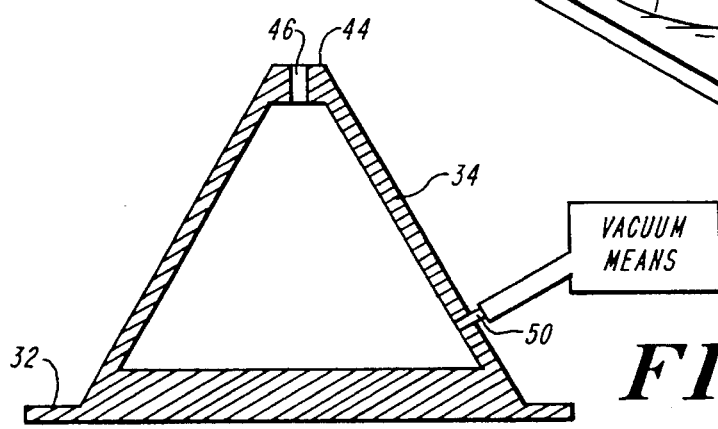
FIG. 6 illustrates a modification of the anesthesia circuit stand of FIG. 2 that is adapted to be connected to a vacuum source.

FIG. 6 illustrates an embodiment in which anesthesia circuit stand 30 is equipped with a vacuum source to ensure the removal of any anesthesia vapors or nitrous oxide from the environment of the operating room. In this embodiment, top surface 44 of distal end 36 of stalk 34 includes an aperture 46 which communicates with an interior chamber 48 within stalk 34. An evacuation port 50 is disposed on the side of stalk 34. Port 50 is able to be connected to a vacuum source (not shown) through a conduit or other means (not shown) to evacuate any gases that may be emitted from the anesthesia circuit.

Figure 7:
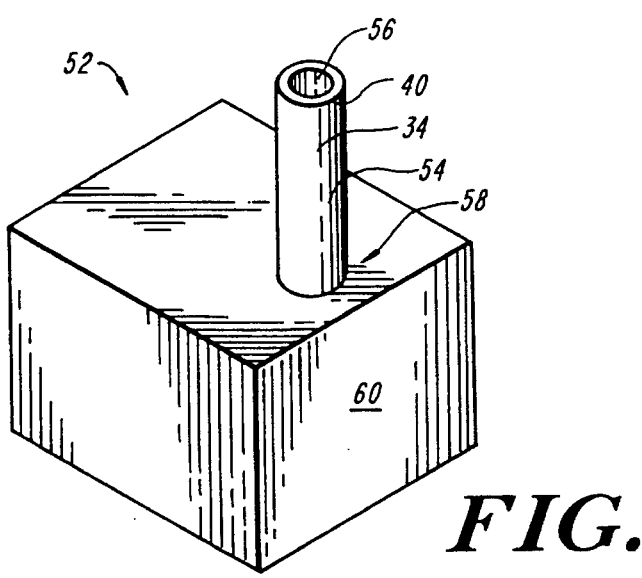
FIG. 7 is a schematic view of an alternative embodiment of an anesthesia circuit stand constructed according to the present invention.

Although stalk element 34 preferably is substantially in the shape of a cone, it is not necessary that such a shape be used. As shown in FIG. 7, an alternative anesthesia circuit stand 52 can take the form of a cylindrical rod 54 of substantially constant diameter. A distal end 56 of rod 54 is configured, as noted above, to engage the inside diameter of anesthesia circuit elbow outlet orifice 22 in an interference fit. The proximal or base end 58 of rod 54 is adapted to securely mount on a stable surface 60, such as an anesthesia machine, a table, or a wall.

The embodiment of FIG. 7 can also be modified to form a free standing anesthesia circuit stand in which a relatively short stalk element 34 is attached to a base (not shown) such as in the form of a disk. This embodiment can be used simply to occlude the outlet orifice 22 with stalk element 34.

The foregoing description of the illustrative embodiments of the invention is presented to indicate the range of constructions to which the invention applies. Variations in the physical architecture and dimensions of the anesthesia circuit stand of the invention will be apparent to those having ordinary skill in the art based upon the disclosure herein, and such variations are considered to be within the scope of the invention in which patent rights are asserted.

What is claimed is:

1. An anesthesia circuit stand device, comprising a base means for securely mounting the stand to a surface;

a stalk element extending from the base means, the stalk element being substantially conical in shape along substantially all of its length, with a proximal end having a diameter that is greater than the diameter of the distal end and said distal end forming a cylindrical plug portion wherein the cylindrical plug portion is solid and the diameter of the cylindrical plug portion is sufficient to fit within the inside diameter of an inhalatory limb of a standard anesthesia circuit elbow in an interference fit that prevents the escape of gas from the anesthesia circuit fitting.

2. The device of claim 1 wherein the base means is integral with the stalk element.

3. The device of claim 1 wherein the base means is secured to the proximal end of the stalk element.

4. The device of claim 1 wherein a top surface of the cylindrical plug portion includes a substantially cylindrical indentation of a diameter substantially less than the diameter of the cylindrical plug portion, the indentation extending into the stalk element for a distance between about 3 and 5 cm.

5. The device of claim 1 wherein the diameter of the cylindrical plug portion is approximately 10.8 to 11.3 mm.

6. The device of claim 1 wherein the base means is adapted to mount on an anesthesia machine.

7. The device of claim 1 wherein the base means is adapted to amount on a rigid, stable surface.

8. The device of claim 1 wherein the diameter of the stalk element ranges from approximately 25 mm at the proximal end to approximately 11.3 mm at the distal end.

9. The device of claim 1 wherein the stalk element has length of approximately 4 to 12 cm.

10. An anesthesia circuit stand device, comprising a base means for securely mounting the stand to a surface;

a stalk element extending from the base means, the stalk element being substantially conical in shape along substantially all of its length, with a proximal end having a diameter that is greater than the diameter of the distal end and said distal end forming a cylindrical plug portion wherein the diameter of the cylindrical plug portion is sufficient to fit within the inside diameter of an inhalatory limb of a standard anesthesia circuit elbow in an interference fit that prevents the escape of gas from the anesthesia circuit fitting and wherein the cylindrical plug portion has an opening, communicating with an open, interior portion of the stalk element;

a port disposed in a side wall of the stalk element, communicating with the open, interior portion of the stalk element; and a means for communicating a vacuum force to the interior portion of the stalk element through the port.

11. A method for preventing the escape of anesthesia gas into the environment of an operating room during delivery of anesthesia gas using an anesthetic circuit technique, comprising the steps of:

providing a stalk element having at a proximal end thereof a stable base and at a distal end thereof a substantially cylindrical plug portion having a diameter sufficient to frictionally fit within the inside diameter of an outlet orifice of an anesthetic circuit fitting of a standard anesthetic circuit;

removing an anesthesia delivery mask from contact with a patient's face;

placing the mask over the stalk element such that the plug portion of the stalk element fits within the inner diameter of the outlet orifice of the anesthetic circuit fitting of the anesthetic circuit in a frictional fit such that anesthesia gas does not escape the seal between the plug portion of the stalk element and the outlet orifice;

pressing the mask away from the outlet orifice toward the proximal end of the stalk element to disengage the frictional connection between the mask and the outside diameter of the outlet orifice; and removing the anesthetic circuit from frictional engagement between the inner diameter of the outlet orifice of the anesthetic circuit and the plug portion of the stalk element.

\* \* \* \* \*